(12) United States Patent
Ward et al.

(10) Patent No.: US 6,277,773 B1
(45) Date of Patent: *Aug. 21, 2001

(54) POLYMERIC MATERIALS

(75) Inventors: Ian Macmillan Ward; Peter John Hine, both of Leeds; Keith Norris, Keighley, all of (GB)

(73) Assignee: BTG International Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/460,239

(22) Filed: Dec. 13, 1999

Related U.S. Application Data

(62) Continuation of application No. 08/790,760, filed on Jan. 27, 1997, now Pat. No. 6,017,834, which is a division of application No. 08/315,680, filed on Sep. 30, 1994, now Pat. No. 5,328,946, which is a continuation of application No. 07/934,500, filed as application No. PCT/GB92/00401 on Mar. 6, 1992, now abandoned.

(30) Foreign Application Priority Data

Mar. 7, 1991 (GB) .................................................. 9104781

(51) Int. Cl.⁷ .............................. D04H 3/14; D04H 1/54; D04H 5/06; B32B 27/14
(52) U.S. Cl. ......................... 442/409; 428/198; 428/229.7
(58) Field of Search .................................. 442/409, 198; 428/297.4, 298.1, 299.7

(56) References Cited

U.S. PATENT DOCUMENTS

| 4,048,364 | 9/1977 | Harding et al. . |
| 4,082,731 | 4/1978 | Knopka . |
| 4,110,391 | 8/1978 | Berzen et al. . |
| 4,228,118 | 10/1980 | Wu et al. . |
| 4,285,748 | 8/1981 | Booker et al. . |
| 4,403,012 | 9/1983 | Harpell . |
| 4,413,110 | 11/1983 | Kavesh et al. . |
| 4,455,527 | 6/1984 | Harpell et al. . |
| 4,483,727 | 11/1984 | Eickman et al. . |
| 4,551,296 | 11/1985 | Kavesh et al. . |
| 4,568,581 | 2/1986 | Peoples, Jr. . |
| 4,786,348 | 11/1988 | Luise . |
| 4,923,660 | 5/1990 | Willenberg et al. . |
| 4,948,661 | 8/1990 | Smith et al. . |
| 4,990,204 | 2/1991 | Krupp et al. . |
| 5,006,390 | 4/1991 | Kavesh et al. . |
| 5,135,604 | 8/1992 | Harpell et al. . |
| 5,244,482 | 9/1993 | Hassenboehler, Jr. et al. . |

FOREIGN PATENT DOCUMENTS

| 0 116 845 | 1/1984 | (EP) . |
| 0 201 029 | 4/1986 | (EP) . |
| 1-48743 | 9/1990 | (JP) . |

*Primary Examiner*—Terrel Morris
*Assistant Examiner*—Ula C. Ruddock
(74) *Attorney, Agent, or Firm*—Nixon & Vanderhye

(57) ABSTRACT

Polymeric monoliths having high stiffness and strength can be produced by heating an assembly of polymer fibres under a contact pressure to a temperature at which a proportion of the fibre is selectively melted and then compressing the assembly. Preferably at least 5% of the polymer is melted so that on compression the molten materials fills the voids within the assembly. The use of polyolefin fibres especially melt spun polyethylene fibres is preferred. The products are useful e.g. as orthodontic brackets, bone prostheses and in body armour.

12 Claims, No Drawings

POLYMERIC MATERIALS

This Application is a Continuation of Ser. No. 08/790,760 filed Jan. 27, 1997, U.S. Pat. No. 6,017,834, which is a divisional of U.S. Pat application Ser. No. 08/315,680, filed Sep. 30, 1994, now U.S. Pat. No. 5,628,946, which is a continuation of U.S. Pat. application Ser. No. 07/934/500, filed Oct. 21, 1992, now abandoned which was filed as PCT/GB92/00401, filed Mar. 6, 1992.

This invention relates to processes for the production of polymer sheet materials from oriented polymer fibres and to the products of such processes.

One method which is widely used to produce high modulus polymer sheets is the formation of fibre reinforced composites using, e.g. oriented polyethylene fibres in order to reinforce the polymer matrix. The manufacture of such composites is a complex operation and in particular requires careful mixing of the polymer and the fibres if the composite is to exhibit homogeneous mechanical properties.

There have been proposals to produce polymeric sheets by compression of networks of polymer fibres at elevated temperatures most notably in relation to thermotropic liquid crystal polymers. European Patent 354285 and U.S. Pat. No. 4,384,016 both describe processes in which fibres of a liquid crystal polymer are hot pressed to produce an oriented polymer sheet. European Patent Application 116845, describes a process in which a network of fibres of ultra-high molecular weight polyethylene are hot compressed to form polymer sheets. In the processes taught in this document the fibres are compressed and heated simultaneously. The products retain a significant proportion of the properties of the fibres in the direction in which the fibres are aligned but the mechanical properties of the products in the direction transverse to that in which the fibres are aligned is less than ideal. These processes are relatively unaffected by the choice of compaction temperature. The polymer fibres do not melt during the process.

We have now discovered a novel process whereby an assembly of fibres of oriented polymer may be hot compressed to form a sheet having superior mechanical properties particularly in the direction transverse to that in which the fibres are aligned. The novel processes are distinguished from those of EPA 116845 by an initial processing step in which the fibres are brought to and held at the compaction temperature whilst subject to a pressure sufficient to maintain the fibres in contact, the contact pressure, and thereafter compacted at a higher pressure, the compaction pressure. In the processes of this invention the compaction temperature does influence the mechanical properties of the compacted product. In the processes of this invention a proportion of the polymer material in the fibres melts and subsequently recrystallises and it is this melt phase which serves to bind the fibres together.

Accordingly from one aspect this invention provides a process for the production of a polymer sheet in which an assembly of oriented polymer fibres is maintained in intimate contact at an elevated temperature sufficient to melt a proportion of the polymer and subsequently compressed so as to produce a coherent polymer sheet.

In the preferred processes of this invention the conditions and more particularly the temperature at which the fibres are compacted will be such as to cause a portion of the polymer to be selectively melted. On cooling the molten materials recrystalise to give a phase with a lower melting point than the original fibre. The presence of a second phase in the compacted product may readily be detected e.g. by D.S.C. measurements. In general the amount of material melted is preferably at least 5% and usually at least 10% of the original. The applicants believe that this minimum amount is required in order fill the spaces between fibres upon compaction and hence produce a product which does not contain trapped air. Processes in which a greater proportion of the polymer material is melted at the contact stage are useful in so far as the mechanical properties of the product in the direction transverse to the alignment of the fibres may be improved but this improvement is achieved at the expense of the properties in the direction of the alignment of the fibres. We have discovered that the improvements in the transverse direction are not directly proportional to the losses in the direction of alignment and that the loss is greater than the improvement. For most applications of the products of this invention the preferred processes are those which are carried out in a manner which selectively melts from 5 to 10% by weight of the polymer material although processes which melt from 10 to 20% by weight of the polymer or even up to 50% by weight may be useful.

In a preferred embodiment the temperature at which the fibres are conpacted is not greater than the peak temperature of melting i.e. the temperature of which the endotherm measured by Differential Scanning Calorimetry (DSC) of the polymer fibres reaches its highest point. The minimum temperature at which the fibres should be contacted is preferably that at which the leading edge of the endotherm extrapolated to zero intersects the temperature axis.

The pressure at which the assembly of fibres is maintained during this stage of the process will be such as to maintain the individual fibres in intimate contact but not such as will compact them and in particular not inhibit the selective melting of the polymer. In general pressures in the range 0.5 to 2.0 MPa are preferred. The precise value is not normally critical.

The compaction pressure exerted upon the heated assembly of oriented polymer fibres should be sufficient to produce a homogeneous product but should not be so great as to cause the assembly to be extruded. If necessary a closed mould may be used to prevent extrusion and thus allows the use of higher temperatures or pressures if required. In general, pressures in the range of 40 to 50 MPa have been found to be useful. The minimum pressure required to process an assembly of a particular polymer fibre at a particular temperature may be determined by routine experiment.

The time required for the processes of this invention may be determined by empirical means. The time required to bring the assembly of fibres up to the requisite temperature will vary with the nature and size of the assembly, the nature of the polymer and the heating means which are employed. The time is not critical provided it is sufficient to enable the selective melting to be achieved.

The time required for the compaction step is also non-critical except in so far as it must be sufficiently long to enable the assembly to be compacted. At the preferred temperatures the minimum time may be of the order of seconds although longer times may be utilised. Processes which utilise shorter compaction times e.g. 5 to 30 seconds may be advantageous in so far as they may conveniently be operated upon a continuous basis for example a uniaxially aligned assembly of heated fibres may be passed between a pair of rollers.

The products of the processes of this invention preferably retain at least 50% and more preferably at least 75% of the mechanical properties, especially the modulus of the oriented fibres in the direction in which those fibres are aligned. The products exhibit a homogeneous appearance to the eye.

Products which when stressed in the direction transverse to that in which the fibres are aligned fibrillate, i.e. break whilst leaving the polymer fibres essentially intact are not homogeneous. The products of this invention exhibit homogeneous behaviour when stressed in this transverse direction. Preferably they will be such that the attenuation of an ultrasonic C scan shows not more than a 20% variation and preferably not more than a 10% variation over the whole sample.

The assembly of oriented polymeric fibres which may be utilised in the processes of this invention may take a variety of forms. In particular they may be arranged as an uniaxially aligned bundle or a twisted bundle of fibres or an assembly of chopped fibres or as a mat of interwoven bundles or a mat formed by layering of bundles of fibres wherein the bundles in each layer are aligned at an angle, e.g. conveniently perpendicular to one another. The products obtained by processing such mats may thus retain the majority of the properties of the oriented fibres in more than one direction. The bundles may be assembled and pressed into any convenient shape. The products may be flat sheets, rods, bars, any of which may be shaped so as to be suitable for particular applications.

The oriented polymer fibres may be obtained by any of the known manufacturing processes. In particular, fibres which have been produced by melt spinning and drawing and gel spinning and drawing. Typically such fibres will have a diameter in the range 0.005 to 0.05 mm.

The processes of this invention may be carried out using conventional equipment. Conveniently, the fibre assembly may be placed in a suitable mould and placed under contact pressure. The assembly may then be preheated to the desired temperature at such a rate as to ensure that there is no significant temperature gradient across the assembly. The desired compaction pressure is then applied and maintained for sufficiently long for the fibres to cohere. The hot compacted materials are preferably cooled to ambient temperature under controlled conditions. Rapid cooling is less preferred. The most convenient techniques is to allow the compacts to stand in the air until they have cooled to ambient temperature.

The processes of the present invention may utilise any polymer fibres which can be selectively melted. The susceptibility of particular polymers and particular grades of that polymer to selective melting varies and their suitability for use in the processes of this invention may be determined empirically.

The processes of the present invention find particular application in the production of oriented polyolefin articles especially oriented polyethylene articles. The polyethylene (which may be a homo or copolymer of polyethylene) may have a weight average molecular weight Mw of from 50,000 to 3,000,000. For polyethylene articles the temperature to which the assembly is preheated is preferably within 5° C. and more preferably within 2° C. of the peak temperature of melting. Oriented polyethylene products of the processes of this invention preferably have a transverse (i.e. in the direction perpendicular to that in which the fibres are aligned) strength of at least 15 MPa and more preferably at least 25 MPa.

Gel spun polyethylenes having a weight average molecular weight of at least 500,000 may exhibit extremely high axial tensile modulus. This corresponds to an extremely high degree of alignment of the polymer molecules within the fibres. These highly oriented gel spun materials may be processed according to this invention and may be preferred where it is desired to produce a product which exhibits high strength in the direction of the fibre alignment. However the strength in the direction transverse to this alignment may be limited unless relatively high proportion of the axial strength is sacrificed by allowing the polymer to melt. Polymer fibres which are not so highly oriented may be preferable in so far as the selective melting which characterises the processes of this invention may affect the axial properties to a lesser degree whilst producing useful strengths in the transverse direction.

Homo and co polymers of polyethylene having a weight average molecular weight of from 50,000 to 500,000 particularly those which can be produced by melt-spinning from a preferred raw material for use in the processes of this invention. Such polymers appear to be more amenable to the selective melting process either by virtue of their comprising some polymer having a relatively low molecular weight or by virtue of their having a surface layer which melts at a lower temperature. Whatever the mechanism which is involved those polymers are preferred because they can form compacts which retain a large proportion of the properties of the fibre (in the direction of alignment of that fibre) whilst producing products having superior properties in the direction transverse to that alignment.

Other classes of polymer fibres which may be useful in the processes of this invention include any of the known orientable polymers. In particular the oriented polymer may be an unsubstituted or mono or poly halo substitued vinyl polymer, an unsubstituted or hydroxy substituted polyester, a polyamide, a polyetherketone or a polyacetal. Suitable examples include vinyl chloride polymers, vinyl fluoride or vinylidene fluoride polymers PHB, PEEK and homo and copolymers of polyoxymethylene. Particular examples of polyesters useful in the processes of this invention include those derivable by the reaction of at least one polyhydric alcohol, e.g. a linear polyhydric alcohol preferably a diol with at least one poly basic acid, suitably a polycarboxylic acid. The alcohol is preferably an alicyclic or aliphatic alcohol such as cyclohexane-dimethanol or a linear alkylene diol such as ethylene glycol, 1,3 propylene glycol or 1,4 butylene glycol. The preferred acids include o, m or ter phthalic acids, 2,6 and 1,5 napthalene dicarboxylic acid and 1,2 dihydroxy benzoic acid.

The compacted products of the present invention normally have a density less than that of the original fibre. This reduction is caused primarily by the retention of air within the compacted material but also by any reduction in the content of crystalline material within the polymer caused by any molten polymer cooling to form an amorphous phase. Both these factors detract from the properties of the product and the preferred processes of this invention produce products in which the density is at least 90% more preferably at least 95% and most preferably substantially the same as that of the polymer fibre. This reflects the fact that the compaction should preferably be carried out in a manner which expels any trapped air from the product and that in the more preferred embodiment the compact will be cooled in a manner which results in the molten material forming a crystalline phase on cooling.

The processes of this invention enable complicated and precisely shaped polymeric articles having high stiffness and high strength to be manufactured. The products may also exhibit good energy absorbing properties. The products find use in a wide variety of applications, particular examples being as orthodontic brackets, as bone implants and as high impact energy absorbing materials, e.g. in body armour.

The invention is illustrated by the following examples:

The tests used in these examples are defined as follows:

The fibre modulus and strength were measured on a 20 cm long sample at a displacement rate of 20 cm/min.

The flexure modulus of the samples produced from the process were measured under the guidelines of ASTM D790.

The flexure strengths of the samples produced from the process were measured under the guidelines of ASTM D790.

The short beam shear strength of the samples measured under the guidelines of ASTM D2344.

The densities of the compacted materials were measured using a density bottle.

Ultrasonic elastic properties were measured using an immersion method at a frequency of 2.25 MHz. A full description of the technique can be found in S. R. A. Dyer, D. Lord, I. J. Hutchinson, I. M. Ward and R. A. Duckett, J. Phys. D:Apply. Phys. 25 (1992) 66.

The fibres used were polyethylene fibres having the following particulars:

| | | Molecular Weight | | | Breaking Strength | Tensile modulus | |
| | | | | | | initial secant | 2% |
| Sample | Fibre | Mw | Mn | Process | GPa | GPa | GPa |
| --- | --- | --- | --- | --- | --- | --- | --- |
| 1 | CELANESE | 61,000 | 28,000 | melt spun | 1.0 | 54 | 36 |
| 2 | SNIA FIBRE | 130,000 | 12,000 | melt spun | 1.3 | 58 | 43 |
| 3 | TEKMILON | 700,000 | 54,000 | solvent spun | 2.1 | 80 | 70 |
| 4 | SPECTRA 1000 | 1,500,000 | 75,000 | gel spun | 2.9 | 130 | 115 |

EXAMPLE 1

A sheet of dimensions 3 mm×5 cm×10 cm was prepared by hot pressing a unidirectionally aligned bundle of melt spun SNIA high modulus polyethylene fibres having a diameter of 0.015 mm in an open ended matched metal mould. The fibres were preheated for 10 minutes under contact pressure of 0.5 MPa at 139±0.5° C. and then a pressure 400 MPa was applied for 10 seconds. The resulting product was a homogeneous translucent sheet with the following properties.

| | | |
| --- | --- | --- |
| Tensile modulus in fibre direction | 57 GPa | measured |
| Transverse to fibre direction | 4.2 GPa | ultrasonically |
| Flexure modulus in fibre direction | 35 GPa | ASTM D790 |
| Transverse to fibre direction | 3.2 GPa | |
| Short beam shear strength | 29 GPa | ASTM D2344 |
| Flexure strength in fibre direction | 110 MPa | ASTM D790 |
| Transverse to fibre direction | 31 MPa | |

An ultrasonic immersion 'C' scan of the product showed only a 2% change in attenuation over the sample and is taken as a measure of the homogeneity of the product.

A DSC trace of the compacted material showed that 8% of the original fibre phase had been melted and had recrystallised forming a second lower melting point phase.

The density of the compacted material was 90% of the original fibre density.

EXAMPLE 2

A bar of 3 mm square cross section was prepared by hot pressing a twisted bundle of melt spun SNIA high modulus polyethylene fibres having a diameter of 0.015 mm in an open ended matched metal mould. The fibres were preheated at 139±0.5° C. for 10 minutes and then pressed for 30 seconds at a pressure of 50 MPa. The resulting product was a homogeneous translucent bar with a flexural modulus (ASTM D790) of 32 GPa.

EXAMPLE 3

An orthotropic material was made by compacting a number of layers of a woven mat of melt spun SNIA high modulus polyethylene fibres in an open ended matched metal mould. The laminated mat was maintained at 139±0.5° C. for 10 minutes at 0.5 MPa before applying a high pressure of 50 MPa for 30 seconds. The flexure modulus was the same in both the axes in the plane of the plate, with a value of 11 GPa. The flexure strength was also similar in the two axes in the plane of the plate with a value of 85 MPa. We can conclude that using a woven mat for compaction results in a substantial improvement in transverse strength at the expense of stiffness.

EXAMPLE 4

A three dimensional shape was formed by compacting a number of layers of a woven mat of melt spun SNIA high modulus polyethylene fibre between male and female hemispherical moulds. The compaction conditions were identical to those shown in example 3. The compacted material was formed into the required shape in a single process.

EXAMPLE 5

A laminated sheet 3 mm thick and 55 mm square was made by sandwiching a uniaxially aligned bundle of melt spun SNIA polyethylene fibres between two layers of a woven mat of melt spun SNIA polyethylene fibres. The sandwich was then compacted using conditions given in example 3. The result was a translucent sheet with the following properties.

| | | |
| --- | --- | --- |
| Tensile modulus in fibre direction | 52 GPa | measured |
| Transverse to main fibre direction | 4.9 GPA | ultrasonically |
| Flexure modulus in main fibre direction | 18 GPa | ASTM D790 |
| Flexure strength transverse to main fibre direction | 75 GPa | ASTM D790 |

Lamination allows a better compromise to be achieve between stiffness and strength, especially in tension.

EXAMPLE 6

2.0 grams of chopped melt spun SNIA high modulus polyethylene fibre was placed in a cylindrical mould which was 12 mm in diameter and 30 mm long. Compaction of the fibre assembly proceeded according to the conditions described in example 3. The resulting cylindrical bar was an isotropic material having a modulus of 5 GPa. A DSC trace of the product showed that 12% of the original fibre had been melted.

EXAMPLE 7

A bar of 25 mm square cross section and 100 mm long was prepared by hot pressing a number of cold compacted layers of melt spun SNIA high modulus polyethylene fibres in a closed matched metal mould using conditions described in example 3. DSC traces taken through the compacted blocks showed that a reasonably even heat distribution had been achieved.

EXAMPLE 8

3.0 grams of melt spun CELANESE high modulus polyethylene fibre with a diameter of 0.015 mm was compacted in an open ended rectangular section steel mould at a compaction temperature of 134±0.5° C. A contact pressure of 0.5 MPa was held for 10 minutes and then a pressure of 40 MPa was applied for 30 seconds. The sample had the appearance of a solid polyethylene rod with a well defined cross section measuring 3.34 mm×3.11 mm. The bending modulus was 19.7 GPa.

EXAMPLE 9

To demonstrate the criticality of the moulding temperature, a sample identical to that used in example 8 was compressed in the same mould at the higher temperature of 138° C. The resulting sample again had the appearance of a solid polyethylene rod but the low bending modulus of 1.2 GPa showed that the properties of the fibre had been lost due to substantial melting of the original fibre phase. Further evidence of the critical nature of the temperature was shown by compressing an identical sample to examples 8 and 9 but at the lower temperature of 127° C. The resulting product had a high stiffness but poor transverse properties due to almost total retention of the original fibre phase.

EXAMPLE 10

The role of pressure was examined by carrying out an identical experiment to example 1 except that high pressure (40 MPa) was applied from the very start of the procedure, including the warm up period. The resulting product had a high longitudinal stiffness of 60 GPa but a poor transverse strength of 12 MPa. A DSC trace of the compacted material showed no evidence of any 'second phase': the compacted material was composed entirely of the original fibre phase.

We can therefore conclude that applying high pressure from the beginning of the compaction process inhibits the selective melting which is necessary for optimum control of the properties of the final product.

EXAMPLE 11

A sheet of dimensions 3 mm×55 mm×55 mm was prepared by compacting a unidirectionally aligned bundle of gel spun SPECTRA high modulus polyethylene fibres in a matched metal mould. The processing conditions were identical to example 3 apart from raising the compaction temperature to 152±0.5° C., which is midway between the onset of melting and the end of melting.

The resulting compacted sheet was homogeneous and had a longitudinal modulus of 35 GPa and a transverse strength of 17 MPa. A DSC trace of the compacted material showed around 35% of a 'second phase' formed by melting of the original fibre.

What is claimed is:

1. A homogeneous polymeric product comprising an assembly of molecularly oriented thermoplastic melt spun, gel spun or solvent spun polymer fibers bound together by a recrystallized melt phase comprising from 5% to 50% by weight of the thermoplastic polymer in the product, wherein both fibers and recrystallized melt phase are derived from the molecularly oriented fibers of a precursor assembly of molecularly oriented thermoplastic melt spun, gel spun or solvent spun polymer fibres.

2. A product according to claim 1 wherein thermoplastic polymer is selected from the group consisting of homo- and copolymers of a polyolefin.

3. A product according to claim 1 wherein said molecularly oriented thermoplastic polymer fibres are polyethylene fibres.

4. A product according to claim 1 wherein said molecularly oriented thermoplastic polymer fibers are fibers of a polymer selected from the group consisting of a vinyl polymer, a polyester, a polyamide, a polyetherketone and a polyacetal.

5. A product according to claim 4 wherein said polymer is polyethylene terephthalate.

6. A product according to claim 1 wherein said recrystallized melt phase is of lower melting point than that of the fiber.

7. A product according to claim 1 wherein the molecularly oriented polymer fibers are fibers that have been melt spun or gel spun and then drawn.

8. A product according to claim 1 wherein the recrystallized melt phase is derived from between 5 to 20% by weight of the oriented polymer fiber.

9. A product as claimed in claim 1 wherein the recrystallized melt phase comprises from 5 to 20% by weight of the thermoplastic polymer.

10. A product according to claim 1 wherein the product is in the form of a polymeric sheet.

11. A product according to claim 1 wherein the product is in the form of a monolith.

12. A product according to claim 1 wherein the fibers are melt spun or gel spun.

* * * * *